United States Patent
Guertin et al.

(10) Patent No.: US 9,932,562 B2
(45) Date of Patent: Apr. 3, 2018

(54) DRAIN DOWN AND RE-FEED OF MICROCARRIER BIOREACTOR

(71) Applicant: GE Healthcare Bio-Sciences Corp., Piscataway, NJ (US)

(72) Inventors: Patrick M. Guertin, Mendon, MA (US); Joseph D. Crowell, South Hamilton, MA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 0 days.

(21) Appl. No.: 14/054,461

(22) Filed: Oct. 15, 2013

(65) Prior Publication Data

US 2014/0106403 A1 Apr. 17, 2014

Related U.S. Application Data

(63) Continuation of application No. 13/355,125, filed on Jan. 20, 2012, now abandoned, which is a continuation of application No. PCT/US2010/043013, filed on Jul. 23, 2010.

(60) Provisional application No. 61/228,026, filed on Jul. 23, 2009.

(51) Int. Cl.
*C12N 7/00* (2006.01)
*C12M 1/12* (2006.01)
*C12M 1/00* (2006.01)

(52) U.S. Cl.
CPC ............ *C12N 7/00* (2013.01); *C12M 25/14* (2013.01); *C12M 47/10* (2013.01); *C12N 2770/24151* (2013.01)

(58) Field of Classification Search
None
See application file for complete search history.

(56) References Cited

U.S. PATENT DOCUMENTS

2003/0143727 A1* 7/2003 Chang ................ 435/289.1
2004/0077086 A1* 4/2004 Reiter et al. .............. 435/404
2006/0073591 A1* 4/2006 Abitorabi et al. ......... 435/404

FOREIGN PATENT DOCUMENTS

WO  WO 03/023021  3/2003
WO  WO 03/029442  4/2003

OTHER PUBLICATIONS

Junker BH et al. Evaluation of a microcarrier process for large-scale cultivation of attenuated hepatitis A. 1992. Cytotechnology. 9:173-187.*
Chu L et al. Industrial choices for protein production by large-scale cell culture. 2001. Current Opinion in Biotechnology. 12:180-187.*
Trabelski, Et.Al. Journal of Biotechnology, vol. 121, No. 2, Jan. 24, 2006 pp. 261-271.
Lee, Et.Al., Biotechnology Progress, vol. 19, No. 2, Apr. 4, 2003 pp. 501-509.
Souza, M., et al., Vaccine, vol. 27, No. 46, 2009, pp. 6420-6423.
Hundt, et al., Vaccine, vol. 25, No. 20, 2007, pp. 3987-3995.

* cited by examiner

*Primary Examiner* — Paul J Holland
(74) *Attorney, Agent, or Firm* — Grogan, Tuccillo & Vanderleeden, LLP

(57) ABSTRACT

The invention provides a method of increasing product yield per culture in a population of product-secreting cells bound to a scaffold, for example, a microcarrier, at least partially immersed in a culture medium in a bioreactor. The method comprising: semi-harvesting product by removing a volume of the culture medium with a first-secreted product concentration while leaving the scaffold with the bound cells in the bioreactor; re-feeding the cells by adding a fresh culture medium to increase the culture medium in the bioreactor to approximately the original volume; agitating the culture medium to allow the cells to grow and release a second-secreted product concentration; harvesting product by removing the culture medium with the second-secreted product concentration while leaving the scaffold with the bound cells behind. Also disclosed is a method of increasing virus yield per culture in a population of virus-infected cells bound to a microcarrier suspended in a culture medium.

7 Claims, No Drawings

DRAIN DOWN AND RE-FEED OF MICROCARRIER BIOREACTOR

RELATED APPLICATIONS

This application is a continuation of U.S. patent application Ser. No. 13/355,125 filed Jan. 20, 2012, abandoned, which is a continuation of International Application No. PCT/US2010/043013, which designated the United States and was filed on Jul. 23, 2010, published in English, which claims priority to U.S. Provisional Patent Application No. 61/228,026, filed on Jul. 23, 2009. The entire teachings of the above applications are incorporated herein by reference.

BACKGROUND

Cell culturing is an essential step in manufacturing biological products such as, for example, nucleic acids, viruses for use in vaccines, antibodies, and proteins, for example, interferons. Anchorage-dependent cells, such as certain animal cells, need to attach to a surface in order to grow and divide.

For large-scale cell culturing, microcarriers provide the large surface area needed for growing anchorage-dependent cells. Van Wezel, in 1967, described the use of microcarriers, small beads or particles approximately 0.2 mm in diameter, for growing such cells. Using gentle agitation, the microcarriers to which the cells will attach are suspended in a liquid culture medium within a bioreactor.

The process may begin with the addition of cells (the inoculum) to the liquid culture medium in which the microcarriers are suspended. The culture medium contains the nutrients essential for metabolism and growth of the cells. Conditions of temperature, pH, and oxygen concentration are controlled to promote cell growth and division in order to increase cell density and confluence.

Continuous or Perfusion Mode: In a continuous or perfusion mode, nutrients are continuously added to the system, and product is harvested throughout the culture period. With the continuous mode, the on-going difficulty in obtaining sufficiently high product titers is well recognized. In addition to the low titer issue, there is a need to concentrate product of the continuous mode. These problems have a direct impact on production time and cost, and make the continuous mode less feasible at least for vaccine production.

Batch Mode: In a batch mode, all nutrients are added at the beginning and products are not removed until the end of the batch. Waste products accumulate during the run, and nutrients are used up, making the batch process inefficient for many applications.

Fed-Batch Mode: A fed-batch mode is similar to the batch mode in that products are removed only at the end of the run, but differs in that nutrients are added at multiple intervals during the process. Most virus-producing, microcarrier cultures are carried out, post infection, in a fed-batch process. In the fed-batch mode, there is also an increase in waste products and other contaminants, such as host cell protein and host cell DNA, and dead cells falling off of the microcarriers.

Thus, there remains an on-going need for a new process that increases product titer while eliminating the problems inherent in the batch mode and the fed-batch mode of cell culturing. Moreover, techniques that can increase the yield, production efficiency or speed of harvesting viral products for vaccines, in particular, would also satisfy an on-going need and permit the health care system to respond more rapidly to new viral outbreaks.

SUMMARY OF THE DISCLOSURE

In contrast to prior art methods for producing virus in mirocarrier cultures, the inventors of the present subject matter have now discovered a new method of harvest and re-feed for culturing, post infection, virus-producing cells on a scaffold such as a microcarrier, a method that significantly increases product titer while reducing the concentration of contaminants in the culture. The disclosed "semi-harvest and re-feed method, also referred to herein as the "drain down and re-feed method," and the "harvest and re-feed method," is also applicable to the culturing of other product-secreting cells on a scaffold, for example a microcarrier, to harvest diverse products, such as antibodies, proteins, hormones, peptides and growth factors. An example of a protein product is an interferon. The invention, inter alia, includes the following, alone or in combination.

In one aspect, the present invention relates to a method of increasing product yield per culture in a population of product-secreting cells bound to a scaffold at least partially immersed in an original volume of a culture medium in a bioreactor, the method comprising: semi-harvesting product by removing from the bioreactor a first portion of the original volume of the culture medium with a first-secreted product concentration from the bioreactor while leaving the scaffold with the bound population of product-secreting cells in the bioreactor; re-feeding the bound population of product-secreting cells by adding to the bioreactor an amount of a fresh culture medium sufficient to increase the volume of the culture medium in the bioreactor to approximately the original volume of the culture medium; agitating the culture medium in the bioreactor under sufficient conditions and for a sufficient time period to allow the bound population of product-secreting cells to grow and to release a second-secreted product concentration into the culture medium; and harvesting product by removing from the bioreactor at least a portion of the culture medium with the second-secreted product concentration from the bioreactor while leaving the scaffold with the bound population of product-secreting cells in the bioreactor. The scaffold can optionally be a microcarrier, e.g., microcarrier beads. This process can continue as long as the cells remain viable to yield third product concentrations, fourth product concentrations, etc.

In another aspect, the present invention relates to a method for increasing virus yield per culture in a population of virus-infected cells bound to a microcarrier suspended in an original volume of a culture medium in a bioreactor, the method comprising: semi-harvesting virus by removing from the bioreactor a first portion of the original volume of the culture medium with a first-shed virus while leaving the microcarrier with the bound population of virus-infected cells and a remaining volume of the culture medium in the bioreactor; re-feeding the bound population of virus-infected cells by adding to the bioreactor an amount of a fresh culture medium sufficient to increase the remaining volume of the culture medium in the bioreactor to approximately the original volume of the culture medium; agitating the culture medium and the microcarrier with the bound population of virus-infected cells under sufficient conditions and for a sufficient time period to allow the virus to continue to infect the bound population of virus-infected cells and to allow the bound population of virus-infected cells to release a second-shed virus into the culture medium; and harvesting virus by removing from the bioreactor at least a portion of the culture medium with the second-shed virus from the bioreactor while leaving the microcarrier with the bound population of virus-infected cells in the bioreactor. Again, this process can be further repeated to yield additional harvests of virus for as long as the virus-infected cells remain viable.

Another embodiment of the invention is a method of increasing virus yield per culture in cells growing on a conditioned microcarrier in a bioreactor, the method comprising: transferring a plurality of seed cells into the bioreactor containing the conditioned microcarrier and an original volume of a culture medium, to form in the bioreactor a mixture comprising the seed cells, the culture medium, and the microcarrier; agitating the mixture in the bioreactor at a sufficient rate of agitation and for a sufficient time to allow the seed cells to bind to the microcarrier; cultivating the seed cells bound to the microcarrier under sufficient conditions and for a sufficient time period for the seed cells to form a bound cell population that is from about 35 percent to about 95 percent confluent on the microcarrier; removing from the bioreactor from about 30 percent to about 88 percent of the original volume of the culture medium in the bioreactor, while leaving the microcarrier with the bound cell population in the bioreactor, to form a first reduced volume of culture medium; infecting the bound cell population with a virus; allowing the virus to adsorb to the bound cell population and to infect the bound cell population; re-feeding the bound cell population including the virus adsorbed thereto by adding to the bioreactor a first amount of a fresh culture medium sufficient to increase the first reduced volume of the culture medium in the bioreactor to approximately the original volume of the culture medium; agitating the culture medium and the microcarrier with the bound cell population under sufficient conditions and for a sufficient time period to allow the virus to infect the bound cell population and to allow the infected, bound cell population to release a first-shed virus into the culture medium; semi-harvesting virus by removing from the bioreactor a portion of the culture medium with the first-shed virus, the portion of the culture medium removed equal to from about 50 percent to about 90 percent of the original volume of the culture medium, while leaving the microcarrier with the infected, bound cell population, and a second reduced volume of the culture medium in the bioreactor; re-feeding the bound cell population by adding to the bioreactor a second amount of a fresh culture medium sufficient to increase the second reduced volume of the culture medium in the bioreactor to approximately the original volume of the culture medium; agitating the culture medium and the microcarrier with the bound cell population in the bioreactor under sufficient conditions and for a sufficient time period to allow the virus to continue to replicate in the bound cell population and to allow the infected, bound cell population to release a second-shed virus into the culture medium in the bioreactor; and harvesting virus by removing from the bioreactor at least a portion of the culture medium with the second-shed virus while leaving the microcarrier with the infected, bound cell population in the bioreactor.

The invention also relates to a method of increasing virus yield per culture in cells growing on a conditioned microcarrier in a bioreactor, the method comprising: transferring a plurality of seed cells into the bioreactor containing a microcarrier and an original volume of a culture medium; cultivating the seed cells to bind to the microcarrier and form a bound cell population that is from about 35 percent to about 95 percent confluent on the microcarrier; removing from the bioreactor from about 30 percent to about 88 percent of the original volume of the culture medium in the bioreactor, while leaving the microcarrier with the bound cell population in the bioreactor, to form a first reduced volume of culture medium; infecting the bound cell population with a virus, which can optionally be a flavivirus; adding fresh culture medium to the bioreactor to maintain the bound cell population; culturing the bound cell population for a sufficient time period to allow the infected, bound cell population to release a shed virus concentration into the culture medium in the bioreactor; and harvesting virus by removing from the bioreactor at least a portion of the culture medium with shed virus therein.

In another aspect of the invention, methods of increasing virus yield per culture in cells growing in a bioreactor are disclosed, comprising the steps of: transferring a plurality of seed cells into the bioreactor containing a support substrate, such as conditioned microcarriers, and an original volume of a culture medium, to form in the bioreactor a mixture comprising the seed cells, the culture medium, and the substrate; and cultivating the seed cells bound to the substrate under sufficient conditions and for a sufficient time period for the seed cells to form a bound cell population that is optionally from about 35 percent to about 95 percent confluent on the substrate.

Once a bound cell population is formed, from about 30 percent to about 88 percent of the original volume of the culture medium in the bioreactor is removed, while leaving the substrate with the bound cell population in the bioreactor, to form a first reduced volume of culture medium; infecting the bound cell population with a virus; allowing the virus to adsorb to the bound cell population and to infect the bound cell population. Fresh culture medium can then be added to the bioreactor and the bound cell population is cultured under sufficient conditions and for a sufficient time period to allow the virus to infect the bound cell population and to allow the infected, bound cell population to release a virus into the culture medium. The virus can then be harvested by the above-described drain down and re-feed method or any other known harvesting techniques.

DETAILED DESCRIPTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The present disclosure relates to the production of cells on microcarriers or other structures for cell attachment, the microcarriers suspended in bioreactors, including, for example, spinner flasks, bench top bioreactors, and larger non-disposable and disposable bioreactors.

Throughout the description and claims of this specification, the words "comprise" and "contain" and variations of these words mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims and abstract), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims and abstract), or to any novel one, or any novel combination, of the steps of any method or process so disclosed.

Typically, in the traditional fed-batch process of growing virally-infected cells, as the culturing of cells progresses, a plateau in viral titer is reached, accompanied by an increase in concentrations of the contaminating host cell protein (HCP), the host cell DNA, and waste products. When the plateau in viral titer is reached, the production of virus has significantly decreased or stopped altogether. At that time, the process is discontinued; the culture medium with shed virus is harvested; the microcarriers with the dead cells are discarded; and a new culture set up. There has been an on-going need to improve this process in order to increase the viral titer achieved within a given period of time, to speed the production of vaccines.

The inventors of the present subject matter have now discovered a new method of culturing anchorage-dependent cells on a scaffold, a method that addresses the potential problem of metabolite depletion and waste product build-up and which provides increased product titer within a given time period as compared to the amount of product titer achieved within the same time period using the fed-batch process. Typically, suspension cultures are maintained in serum free media.

The disclosed method provides for a supply of specific nutrients, growth factors, lipids, amino acids, vitamins, salts, and trace metals by increasing their relative concentration during culture to an optimal level, and removing contaminants, thus improving not only the cell growth rates, but also culture density, specific productivity and/or specific product quality and concentration.

An embodiment of the invention provides a "drain-down" or "semi-harvest and re-feed" step that significantly reduces the concentration of metabolic waste products and cellular byproducts such as host cell protein and host cell DNA. Host cell protein and host cell DNA are contaminants that interfere with production of a virus for use in a vaccine, for example. The drain-down step can remove a large portion of the contaminated culture medium, and the re-feed step replenishes the nutrient-depleted, contaminated culture medium by adding fresh medium.

In one aspect, the invention provides for the use of a harvest or semi-harvest and re-feed of an infected attachment culture, including, but not limited to virus-producing microcarrier cultures, in order to increase virus titer, for example. In another aspect, the invention provides for increasing product yield per culture in a population of product-secreting cells bound to a scaffold.

Disclosed herein is a method for sterilely removing a volume of the conditioned culture medium, for example, the removal of about seventy-five percent (75%) of the culture medium, while retaining in the bioreactor the total cell population bound to a microcarrier. This semi-harvest is followed by replacement with an equal volume of fresh culture medium. The culturing process is allowed to continue.

As the terms are used, herein, "semi-harvest" and "harvest" have substantially the same meaning and are sometimes used interchangeably. "Semi-harvest" is often used to denote a step in which the culture medium is drained down, for example, using a sieve, to collect the virus that was shed into the culture medium during an early phase of the culturing process. "Harvest" is generally used herein to denote the final drain-down of the culture medium to collect the virus shed during a later phase of the culturing process. The final harvest is typically done when the cytopathic effect (CPE) is from about 60 percent to about 90 percent, or at about 80 percent. As the terms are used herein, a "liter" is denoted by "L" and a milliliter or cubic centimeter is denoted by "ml".

One embodiment of the present invention relates to a method of increasing product yield per culture in a population of product-secreting cells bound to a scaffold immersed in a culture medium in a bioreactor. The scaffold can optionally be a microcarrier, such as microcarrier beads. The method includes: semi-harvesting the product by removing a first portion of the culture medium which includes a first-secreted product concentration, while leaving the scaffold with the bound population of product-secreting cells behind in the bioreactor; then re-feeding the bound population of product-secreting cells by adding fresh culture medium in an amount sufficient to increase the volume of the culture medium to approximately the original volume of the culture medium. Next, the culture medium in the bioreactor is agitated under sufficient conditions and for a sufficient time period to allow the bound population of product-secreting cells to grow and to release a second-secreted product concentration into the culture medium. Finally, when product titers have approximately peaked, the product is harvested by removing from the bioreactor at least a portion of the culture medium with the second-secreted product concentration from the bioreactor while leaving the scaffold with the bound population of product-secreting cells in the bioreactor.

Another embodiment of the present invention is a method for increasing virus yield per culture in a population of virus-infected cells bound to a microcarrier suspended in an original volume of a culture medium in a bioreactor. This embodiment of the method includes: semi-harvesting virus by removing a first portion of the original volume of the culture medium with a first-shed virus while leaving the microcarrier with the bound population of virus-infected cells and a remaining volume of the culture medium in the bioreactor; then re-feeding the bound population of virus-infected cells by adding to the bioreactor an amount of a fresh culture medium sufficient to increase the remaining volume of the culture medium in the bioreactor to approximately the original volume of the culture medium; then agitating the culture medium and the microcarrier with the bound population of virus-infected cells under sufficient conditions and for a sufficient time period to allow the virus to continue to infect the bound population of virus-infected cells and to allow the infected, bound population of virus-infected cells to release a second-shed virus into the culture medium. Finally, at the time of approximately peak titers, virus is harvested by removing culture medium with the second-shed virus from the bioreactor while leaving the microcarrier with the infected, bound population of virus-infected cells in the bioreactor.

In yet another embodiment is a method of increasing virus yield per culture in cells growing on a conditioned microcarrier in a bioreactor, the method including: transferring a plurality of seed cells into the bioreactor containing the conditioned microcarrier and an original volume of a culture medium. The bioreactor at this point contains a mixture comprising the seed cells, the culture medium, and the microcarrier. The mixture in the bioreactor is agitated at a sufficient rate and for a sufficient time to allow the seed cells to bind to the microcarrier. The bound seed cells are cultivated under sufficient conditions and for a sufficient time period for the seed cells to form a bound cell population that is from about 35 percent to about 95 percent confluent on the microcarrier. At this time a drain-down or semi-harvest is performed, thereby removing from the bioreactor from about 30 percent to about 88 percent of the original volume of the culture medium in the bioreactor, while leaving the microcarrier with the bound cell population in the bioreactor. There is now a first reduced volume of culture medium in the bioreactor. The bound cell population is infected with a virus, which is allowed to adsorb to the bound cell population and to infect the bound cell population. Then the bound cell population including the virus adsorbed thereto is re-fed with fresh medium, by adding first amount of a fresh culture medium sufficient to increase the first reduced volume of the culture medium in the bioreactor to approximately the original volume of the culture medium. Again the culture medium and the microcarrier with the bound cell population is agitated under sufficient conditions and for a sufficient time period to allow the virus to infect the bound cell population and to allow the infected, bound cell population to release a first-shed virus into the culture medium.

The virus is then semi-harvested by removing from the bioreactor a portion of the culture medium with the first-shed virus, the portion of the culture medium removed equal to from about 50 percent to about 90 percent of the original volume of the culture medium, while leaving the microcarrier with the infected, bound cell population, and a second reduced volume of the culture medium in the bioreactor. Then the bound cell population is re-fed by adding a second amount of a fresh culture medium sufficient to increase the second reduced volume of the culture medium in the bioreactor to approximately the original volume of the culture medium. Agitating the culture medium and the microcarrier with the bound cell population is continued under sufficient conditions and for a sufficient time period to allow the virus to continue to infect the bound cell population and to allow the infected, bound cell population to release a second-shed virus into the culture medium in the bioreactor. Finally, the virus is harvested by removing the culture medium with the second-shed virus while leaving the microcarrier with the infected, bound cell population in the bioreactor.

In the foregoing example, the semi-harvesting of the virus may comprise removing about 75 percent of the culture medium with the first-shed virus from the bioreactor.

In any of the above-described examples, the bioreactor may be, for example, a disposable or a non-disposable bioreactor having a volume of from about 25 liters to about 200 liters. In another embodiment, bioreactor is chosen from a bench-top bioreactor and a spinner flask.

In some embodiments, the cells cultured are VERO cells.

The term "virus" as used herein is intended to cover not only complete infectious viral particles but also any other secreted products that can be used to immunize a subject, including for example, attenuated viruses, genetically engineering viruses that are defective, e.g., in their envelope, nucleocapsid, or genome, viral fragments and any other viral derivatives suitable for use in vaccines or screening assays. In some embodiments, the virus is a Flavivirus. Examples of Flaviviruses include: St. Louis encephalitis, Japanese encephalitis, tick-borne encephalitis viruses, dengue virus, Kyasanur Forest disease virus, and Yellow Fever virus.

EXEMPLIFICATION

Example 1: Benchtop Bioreactor Production with Microcarriers and VERO Cells

SUMMARY: Using a 10 L New Brunswick (NBS) benchtop bioreactor operating at 8 L culture volume with 5 g/L microcarriers, we prepared HYPERFLASK® (CORNING®, Corning N.Y.) seed cultures and the benchtop bioreactor; performed infection, semi-harvest and re-feed on the bioreactor.

Pre-Seed Preparation:
Set-up (8) HYPERFLASKS®, inoculated approximately 1:6 from (1 or 2) confluent HYPERFLASKS®, incubated at 37° C. in humidified 5% $CO_2$ incubator.

Benchtop Bioreactor and Microcarrier Preparation:
a. Prepared 40 grams of CYTODEX® I microcarriers (GE Healthcare Bio-Sciences AB, Uppsala, SWEDEN) by hydrating more than 4 hours in Phosphate buffered saline (PBS) (50 mL/g beads). Note: 1 g beads swells to 20 mL volume.
b. Following hydration, aspirated the hydrating PBS and replaced with fresh PBS.
c. Autoclaved beads at 123° C. for 60 min liquid cycle.
d. Prepared 10 liter benchtop bioreactor, that is, calibrated probes, assembled tubing and interior harvest sieve tube.
e. Autoclaved bioreactor at 121° C. for 60 min liquid cycle.
f. Allowed to cool in BioSafety cabinet (BSC).
g. From microcarriers, aspirated PBS; introduced 3 L culture medium (OPTIPRO™, glucose, salts, serum-free medium—Invitrogen, Carlsbad, Calif.).
h. Mixed, allowed to settle, let stand at least 1 hour. Then aspirated medium. Introduced fresh medium up to 2 L volume.
i. Sterily introduced approximately 6.8 L of culture medium into the bioreactor.
j. Sterily transferred the conditioned microcarriers into the bioreactor and allowed to mix, agitating at about 50 rpm for approximately an hour in order to allow the reactor to equilibrate.

Benchtop Bioreactor Seeding (21 Sep. 2008):
a. Harvested cells from (8) confluent HYPERFLASKS®. The harvest volume was approximately 1.2 L. Performed cell count.
b. Introduced the seed suspension into the awaiting bioreactor. This resulted in a final initial viable cell (VC) density of approximately 4E5VC/mL after the reactor is Quantity Sufficient (QS) to 8 L final volume.
c. Agitated at 50 rpm for 1 minute in order to mix cells and beads.
d. Stopped agitation for approximately 30 minutes.
e. Agitated at 50 rpm for 1 minute.
f. Stopped agitation for approximately 30 minutes.
g. Agitated at 50 rpm for about 5 minutes. Pulled sample for visual examination to ensure cell attachment to the beads.
h. Attachment was apparent, and therefore, then cultivation and reactor parameters were set.

i. Sampled daily for visual observation, metabolite analysis and nuclei count. After several days of cultivation, when beads were 70-80% confluent, the culture was ready for infection with viral stock.

Infection Procedure:
a. Viral Stock
  i. Obtained attenuated Yellow Fever viral stock from −80° C. storage. Allowed to thaw at room temperature.
  ii. In a BSC, introduced appropriate amount of viral stock into 100 mL of serum free medium (OPTIPRO™, Invitrogen, Carlsbad, Calif.) in transfer apparatus, amount appropriate in order to achieve target Multiplicity Of Infection (MOI), that is, ratio of infectious virus particles to Vero cells, equal to about 0.01.
b. Bioreactor Readiness
  i. Turned off agitation and other parameter controls on the bioreactor and allowed the beads with cells to settle.

ii. Once settled, aseptically removed approximately 7 L of medium via the sieve tube, avoiding the removal of beads. (Needed to remove from about 40 percent to about 88 percent of medium).

iii. Introduced the above referenced viral stock (step 4.a.i).

iv. Once introduced, returned the transfer apparatus to the BSC and added 100 ml medium in order to chase viral stock in transfer line into the reactor completely.

v. Turned on agitation at 30 rpm with other parameter controls off for 1 hour.

vi. After 1 hour, introduced fresh medium up to the 8 L volume and increased agitation to 50 rpm and turned on all parameter controls to the original settings.

Drain-Down/Semi-Harvest and Re-Feed of Infected Culture (30 Sep. 2008):

a. Following approx. 9 days of cultivations and monitoring, drained down or semi-harvested the conditioned medium containing the first-shed virus.

i. Turned off agitation and other parameter controls on the bioreactor and allowed the beads/cells to settle.

ii. Once settled, aseptically drained down approximately 6 L of medium via the sieve tube, avoiding the removal of beads.

iii. After draining down of conditioned medium with first-shed virus, introduced fresh medium up to the 8 L total volume and increased agitation to 50 rpm and turn on all parameter controls to the original settings.

Final Harvest: Second-Shed Virus (4 Oct. 2008)

Following approx. 4 days of cultivations and monitoring, harvested the conditioned medium containing the second-shed virus.

i. Turned off agitation and other parameter controls on the bioreactor and allowed the beads/cells to settle.

ii. Once settled, aseptically drained down approximately 90 percent of medium via the sieve tube, avoiding the removal of beads.

iii. Plaque Forming assay performed. Viral titer obtained was 7.25 E+06 Plaque Forming Units (PFU) per ml. The results are displayed in TABLE 1 below.

Example 2: Spinner Flask Production with CYTODEX® I Microcarriers and VERO Cells Summary: Prepared (12) T-150 flasks. Seeded (2) 500 mL seed spinner flasks (300 mL working volume) each at approximately 4 E+05 VERO CELLS/ml (VC/mL) and 5 g/L microcarrier beads, respectively. (This is done to provide a theoretical value of 18.6 cells/bead). Used each seed spinner culture to inoculate each of (2) "receiving" spinner flask cultures, all at 4 E+05 VC/mL and 5 g/L microcarriers, respectively.

1) Pre-Seed Preparation:

a. Set-up (12) T-150 flasks inoculated 1:6 from (2) confluent T-150 flasks. Incubated at 37° C. for approximately 72 hours.

2) Seed Spinner Flask and Microcarrier Preparation:

a. Prepared 3 grams of CYTODEX® I microcarriers by hydrating >4 hours in PBS (50 mL/g beads). Note: 1 g beads swells to 20 mL volume.

b. Following hydration, aspirated hydrating PBS and replaced with fresh PBS.

c. Autoclaved at 123° C. for 60 min liquid cycle.

d. Allowed to cool in BSC. Aspirated PBS and introduced 300 mL VP-SFM medium.

e. Mixed; allowed to settle, letting stand at least 1 hour. Then aspirated medium. Introduced fresh medium up to 200 mL volume.

f. Aliquoted 100 mL of medium with 1.5 g of beads (should be ~30 mL bead volume) into each of (2) 500 mL spinner flasks. Placed in 37° C. incubator at 40 rpm and allowed to equilibrate for >1 hour.

3) Seed Spinner Inoculation:

a. Harvested cells from (12) confluent T-150 flasks. The harvest volume was approximately 150 mL. Performed cell count.

b. Aliquoted volume (approximately 75 mL) of cells suspension equal to approximately 1.2E8 total viable cells (VC) into each of (2) seed spinners flasks (reference above 2f). This resulted in a final initial viable cell density of approximately 4E5 VC/mL after the spinners are QS to 300 mL final spinner volume each.

c. Placed in 37° C. incubator. Agitated at 40 rpm for 1 minute in order to mix cells and beads.

d. Stopped agitation for approximately 30 minutes.

e. Agitated at 40 rpm for 1 minute.

f. Stopped agitation for approximately 30 minutes.

g. Agitated at 40 rpm. Moved flask to the hood and pulled sample for visual examination to ensure cell attachment to the beads.

h. Attachment was apparent, and therefore, then each spinner flask was brought to QS-300 mL with warm VP-SFM medium. If no attachment, we would have repeated steps 3d-g.

i. Returned spinner flask to the incubator and turned on agitation at 50 rpm.

j. Sampled daily for visual observation, metabolite analysis and nuclei count.

k. When beads were 70-80% confluent, the culture was ready for use in seeding next flasks.

l. Note: Each seed spinner flask should be sufficient to seed (2) subsequent flasks as described below.

4) Receiving Spinner Flask and Microcarrier Preparation:

a. Prepared 6 grams of CYTODEX® I microcarriers by hydrating >4 hours in PBS (50 mL PBS/g beads). Note: 1 g beads swells to 20 mL volume. This was enough to prepare (4) 500 mL spinner flasks at 400 mL final culture volume.

b. Following hydration, aspirated hydrating PBS and replaced with fresh PBS.

c. Autoclaved at 123° C. for 60 min liquid cycle. Caution with Handling.

d. Allowed to cool in BSC, then aspirated PBS and introduced VP-SFM medium to a 400 mL total volume.
e. Mixed and allowed to settle, letting stand at least 1 hour. Then aspirated medium. Introduced fresh medium up to 400 mL volume.
f. Aliquoted 100 mL of medium with 1.5 g of beads (should be ~30 mL bead volume) into each of the 500 mL spinner flasks. Placed them in 37° C. incubator at 40 rpm and allowed to equilibrate for >1 hour.

5) TrypLE™ (Invitrogen) Experimental Spinners Set-Up:
a. Transferred (1) of the above referenced seed spinner flasks (reference 3j) into the BSC.
b. Allowed to settle, then aspirated medium.
c. Introduced 100 mL PBS and gently swirled to mix.
d. Allowed to settle and aspirated PBS.
e. Introduced 40 mL TrypLE™ (Invitrogen) to each flask. Gently swirled to mix. Transferred flask into 37° C. incubator and agitated at 40 rpm for 10 minutes.
f. Transferred (2) of the above referenced "receiving" spinner flasks (reference 4f) into the BSC.
g. Removed seed spinner from incubator and in BSC introduced 100 mL medium. Returned to incubator and agitated at 60 rpm for 2 min.
h. In BSC, swirled the seed flask to ensure uniform suspension. Aliquoted approximately 44 mL into each of awaiting "receiving" flasks (reference 6f).
i. Placed each in 37° C. incubator. Agitated at 40 rpm for 1 minute in order to mix cells and beads.
j. Stopped agitation for approximately 30 minutes.
k. Agitated at 40 rpm for 1 minute.
l. Stopped agitation for approximately 30 minutes.
m. Agitated at 40 rpm. Moved flask to the hood and pulled sample for visual examination to ensure cell attachment to the beads.
n. Attachment was apparent. Then QS each spinner flask to 400 mL with warm VP-SFM™ (Invitrogen, Carlsbad, Calif.) serum free medium. (If not QS, we would have repeated steps 6j-m.) To QS to 400 mL final volume, this means adding approximately 256 mL fresh medium.
o. Returned spinner flask to the incubator and turned on agitation at 50 rpm.
p. Sampled daily for visual observation, metabolite analysis, nuclei count and trypsin count for viability determination.

Results for Example 1: Benchtop Bioreactor Production with Microcarriers and VERO Cells The results of the Example 1 test run of the disclosed drain-down and re-feed method, as performed in a 10 Liter bench top bioreactor are shown in the Table below. The Table shows the viral count in plaque forming units (PFU) at Time zero at 2.50 E+02, and reaching a peak of 1.15 E+08 at 48 hours, then decreasing to 1.01 E+07 at 96 hours. The best time to harvest would have been at the peak titer, reached at 48 hours.

In subsequent cultures utilizing the disclosed method, we typically seeded the microcarriers at from about 4 E+05 VC/ml to about 6 E+05 VC/ml. We then typically infected at about 48 hours post-seed, when the cells are about 85 percent (85%) confluent. Infection may also be done when the bound cell population is from about 35 percent to about 95 percent confluent on the microcarrier. In one embodiment of the invention, at infection, the concentration of cells is greater than or equal to about 7E5 VC/ml.

We generally perform a drain-down or semi-harvest and re-feed at about 72 hours post infection. The final harvest is usually carried out at about 52 hours post re-feed. The best concentration of viable cells seeded on the microcarriers, and the best times for infecting, drain-down, and final harvest will of course vary with the type of virus used, and can be determined without undue experimentation by those of skill in the art.

The VERO host cell protein and DNA are also shown in the Table.

Analysis: By using the above-disclosed drain-down and re-feed method, we were able to obtain approximately 10 percent (10%) greater viral titer in a time period of about seven (7) days than the viral titer we obtained with the traditional fed-batch process in a similar time period. This was an unexpected result, but a fortunate outcome because the disclosed method achieves a significant savings in cost of vaccine production over the fed-batch method and a significant savings in time. When vaccines are needed urgently, the disclosed method can help to speed production of the vaccines. The levels of host cell protein and DNA contaminants are also lowered when using the disclosed method rather than the batch fed method.

We are also performing the disclosed method in a 200 Liter bioreactor and plan to scale up to a 500 liter bioreactor.

TABLE

| Sample number | Sample description | Plaque assay Expt # | PFU/ml | DNA assay Expt # | DNA/ml by picogreen assay µg/mL | Vero protein Expt # | Vero cell protein/ml by ELISA µg/mL |
|---|---|---|---|---|---|---|---|
| Y0183A T-0 | T-0 (Infection) | Y0190A | 2.50E+02 | Y0199A | 0.23 | Y0188A | 18.392 |
| Y0183A | 24 Hr | Y0190A | 2.50E+04 | Y0199A | 0.18 | Y0188A | 14.757 |
| Y0183A | 48 Hr | Y0190A | 2.50E+04 | Y0199A | 0.26 | Y0188A | 25.068 |
| Y0183A | 72 Hr | Y0190A | 5.00E+05 | Y0199A | 0.34 | Y0188A | 30.752 |
| Y0183A | 96 Hr (Drain down) | Y0190A | 1.01E+07 | Y0199A | 0.47 | Y0188A | 48.819 |
| Y0183A (A) | T-0 (One hour after Re-Feed) 30 Sep. 2008 | Y0213A | 7.25E+06 | Y0206A | 0.39 | Y0205A | 25.445 |
| Y0183A (A) | 24 Hr | Y0213A | 8.50E+07 | Y0206A | 0.3 | Y0205A | 34.106 |
| Y0183A (A) | 48 Hr | Y0213A | 1.15E+08 | Y0206A | 0.69 | Y0205A | 63.131 |
| Y0183A (A) | 72 Hr | Y0213A | 2.05E+07 | Y0206A | 1.2 | Y0205A | 95.818 |
| Y0183A (A) | 96 Hr | Y0213A | 7.25E+06 | Y0206A | 1.4 | Y0205A | 147.463 |

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed:

1. A method of enhancing production of a product from a cell culture of product-secreting cells bound to a microcarrier, the method comprising:
   culturing by agitation via rotation a population of cells bound to a microcarrier suspended within an original volume of a culture medium in a bioreactor during a first culture phase to allow the bound population of product-secreting cells to grow and to release a first-secreted product concentration into the culture medium;
   semi-harvesting product by removing from the bioreactor a first portion of the original volume of the culture medium with a first-secreted product concentration from the bioreactor, the first portion removed equal to from 50 percent to 90 percent of the original volume of the culture medium, while leaving the microcarrier with the bound population of product-secreting cells and a remaining volume of culture medium in the bioreactor;
   re-feeding the bound population of product-secreting cells by adding to the bioreactor an amount of a fresh culture medium sufficient to increase the volume of the culture medium in the bioreactor to approximately the original volume of the culture medium;
   agitating via rotation the culture medium and microcarrier in the bioreactor under sufficient conditions and for a sufficient time period to suspend the microcarrier within the culture medium while allowing the bound population of product-secreting cells to grow and to release a second-secreted product concentration into the culture medium, wherein the culture medium is maintained at approximately the original volume during the second culture phase; and
   harvesting product by removing from the bioreactor at least a portion of the culture medium with the second-secreted product concentration from the bioreactor while leaving the microcarrier with the bound population of product-secreting cells in the bioreactor
   whereby the semi-harvesting and harvesting steps yield increased product relative to a fed-batch process under similar conditions; and
   wherein at all times during the semi-harvesting, re-feeding, agitating and harvesting steps the bound population of product-secreting cells remains within the culture medium in the bioreactor.

2. The method of claim 1, wherein the product is chosen from a virus, an antibody, a growth factor, a protein, a peptide, and a hormone.

3. The method of claim 1, wherein the product is a virus and the virus is optionally a flavivirus.

4. A method of enhancing virus production in cells growing on a conditioned microcarrier in a bioreactor, the method comprising:
   transferring a plurality of seed cells into the bioreactor containing a microcarrier and an original volume of a culture medium,
   agitating via rotation a mixture in the bioreactor at a sufficient rate of agitation and for a sufficient time to allow the seed cells to bind to the microcarrier;
   cultivating the seed cells to bind to the microcarrier by agitation via rotation and form a bound cell population that is from 35 percent to 95 percent confluent on the microcarrier;
   removing from the bioreactor from 30 percent to 88 percent of the original volume of the culture medium in the bioreactor, while leaving the microcarrier with the bound cell population in the bioreactor, to form a first reduced volume of culture medium;
   infecting the bound cell population with a virus, which can optionally be a flavivirus;
   adding fresh culture medium to the bioreactor to maintain the bound cell population;
   agitating via rotation the culture medium to suspend the microcarrier and bound cell population within the culture medium;
   culturing by agitation via rotation the bound cell population for a sufficient time period to allow the infected, bound cell population on the suspended microcarrier to release a shed virus concentration into the culture medium in the bioreactor;
   semi-harvesting virus by removing from the bioreactor at least a portion of the culture medium with shed virus therein, the portion removed equal to from 50 percent to 90 percent of the original volume of the culture medium;
   re-feeding the bound cell population by adding to the bioreactor a second amount of a fresh culture medium sufficient to increase the second reduced volume of the culture medium in the bioreactor to approximately the original volume of the culture medium;
   culturing by agitation via rotation the bound cell population in the bioreactor under sufficient conditions and for a sufficient time period to allow the virus to allow the infected, bound cell population to release a second-shed virus into the culture medium in the bioreactor; and
   harvesting virus by removing from the bioreactor at least a portion of the culture medium with the second-shed virus while leaving the microcarrier with the infected, bound cell population in the bioreactor
   whereby the semi-harvesting and harvesting steps yield increased amount of virus relative to a fed-batch process under similar conditions; and
   wherein at all times during the semi-harvesting, re-feeding, culturing by agitation and harvesting steps the microcarrier with the infected, bound cell population remains at least partially immersed within the culture medium in the bioreactor.

5. The method of claim 4, wherein the semi-harvesting of virus comprises removing 65 percent to 75 percent of the culture medium with the first-shed virus from the bioreactor.

6. The method of claim 4, wherein the infecting of the bound cell population with a virus is performed when the bound cell population is at least 85 percent confluent on the microcarrier.

7. The method of claim 1, wherein the cells are anchorage-dependent mammalian cells and optionally are VERO cells.

* * * * *